United States Patent [19]

Ryan

[11] Patent Number: 4,764,024

[45] Date of Patent: Aug. 16, 1988

[54] STEAM TRAP MONITOR

[75] Inventor: Michael J. Ryan, Plainfield, Ill.

[73] Assignee: The United States of America as represented by the United States Department of Energy, Washington, D.C.

[21] Appl. No.: 45,960

[22] Filed: May 4, 1987

[51] Int. Cl.[4] .................. G01K 11/00; G01N 25/20
[52] U.S. Cl. ............................ 374/39; 237/67; 73/200
[58] Field of Search ............... 374/39, 40, 24; 73/200

[56] References Cited

U.S. PATENT DOCUMENTS

| | | | |
|---|---|---|---|
| 1,267,757 | 5/1918 | Gibson | 374/41 |
| 3,167,957 | 2/1965 | Ziviani | 374/39 |
| 3,631,717 | 1/1972 | Kato | 374/40 |
| 3,970,832 | 7/1976 | Itschner . | |
| 4,157,034 | 6/1979 | Buchele . | |
| 4,198,859 | 4/1980 | Holtermann . | |
| 4,456,173 | 6/1984 | Miner et al. | 73/200 X |
| 4,542,993 | 9/1985 | Mims et al. . | |
| 4,547,078 | 10/1985 | Long et al. . | |
| 4,561,785 | 12/1985 | Long et al. . | |
| 4,618,266 | 10/1986 | Feller . | |

OTHER PUBLICATIONS

Article in Plant Engineering, entitled "Checking Steam Trap Operation", File 3580, Feb. 12, 1987, pp. 38–42.

Primary Examiner—Daniel M. Yasich
Attorney, Agent, or Firm—Hugh W. Glenn; Robert J. Fisher; Judson R. Hightower

[57] ABSTRACT

A steam trap monitor positioned downstream of a steam trap in a closed steam system includes a first sensor (the combination of a hot finger and thermocouple well) for measuring the energy of condensate and a second sensor (a cold finger) for measuring the total energy of condensate and steam in the line. The hot finger includes one or more thermocouples for detecting condensate level and energy, while the cold finger contains a liquid with a lower boiling temperature than that of water. Vapor pressure from the liquid is used to do work such as displacing a piston or bellows in providing an indication of total energy (steam+condensate) of the system. Processing means coupled to and responsive to outputs from the thermocouple well hot and cold fingers subtracts the condensate energy as measured by the hot finger and thermocouple well from the total energy as measured by the cold finger to provide an indication of the presence of steam downstream from the trap indicating that the steam trap is malfunctioning.

22 Claims, 3 Drawing Sheets

STEAM TRAP MONITOR

CONTRACTUAL ORIGIN OF THE INVENTION

The United States Government has rights in this invention under Contract No. W-31-109-ENG-38 between the U.S. Department of Energy and the University of Chicago, representing Argonne National Laboratory.

BACKGROUND OF THE INVENTION

This invention relates generally to the detection of energy losses in a steam system and is particularly directed to a steam trap monitor for detecting leaks in a steam trap.

Energy is lost from steam systems in various ways such as conduction, convection, and radiation. Additional losses may occur becuase of leaks such as in the joints of the piping system or because of faulty or permanently open bypasses. Some of the losses, such as pipe ruptures, blown gaskets, and other failures of pressure system integrity, are easily detected. Other losses are more difficult to detect and frequently go unnoticed.

One source of steam loss difficult to detect is that of the failed steam trap. Steam traps are incorporated in a steam system to remove condensate and air from the system while retaining live steam for use in a process. The condensate removed by a steam trap is returned to the heating source for re-heating to be again converted into steam. Traps can fail in either the open or closed position. Failure in the closed position is more likely to be noticed because it usually interrupts the process. Failure of a trap in the open position results in an abnormal amount of heat loss from the system, and may also cause a pressure loss affecting other parts of the steam system. Estimates of the number of failed steam traps, based on plant surveys, vary between 20 and 60 percent. Indeed, one expert maintains that after three years all steam traps are suspect and are very likely to have failed because of wear or contamination.

The use of an ultrasonic listening device is the most commonly used method for determining if a trap is working correctly. This method involves listening to a steam trap during operation to determine if it is working correctly. Each of the several types of steam traps exhibits a distinct sound. However, it is extremely difficult to detect leakage from a trap which is still operative. In addition, certain types of traps, e.g., the float-type steam trap, are frequently in a steady state mode rendering it extremely difficult to acoustically detect a malfunction. However, the sound test method offers advantages over visual checking of the steam trap, particularly where direct visual observation of the discharge from a trap is not possible such as when the steam trap discharge is piped into a closed condensate return system. A third steam trap checking approach involving temperature measurements either upstream or downstream of or within the stream trap is generally considered to be totally unreliable and has resulted in the rejection of large numbers of perfectly good traps and the overlooking of probably an equal number of faulty steam traps left in service.

Increased energy costs in combination with the aforementioned limitations of existing steam trap checking methods have led to the introduction of mechanical devices for monitoring steam trap operation. One approach employs a sensing unit positioned upstream from the steam trap for sensing the normal buildup of condensation. The absence of condensate indicates steam trap failure in the open position. Another available detector, also mounted upsteam of the trap, includes an internal weir which lowers the level of condensate when steam is being discharged by the trap. The absence of condensate at the tip of a probe indicates that the trap has failed and should be removed from service, cleaned, or repaired. A third device, integral with the steam trap itself, senses dynamic flow conditions through the discharge port with trap discharge resulting in movement of a spool exposed to the flow stream causing magnetic displacement of an external indicator ring. Each of these three devices is illustrated and briefly described in an article entitled "Checking Steam Trap Operation", in *Plant Engineering,* File 3580, Feb. 12, 1987, pp. 38–42.

Saturated steam and water at the same pressure have the same temperature. Therefore, the use of the aforementioned prior art temperature sensing devices alone will not detect the presence of both phases (water and steam) downstream from a steam trap. In addition, these prior art temperature sensitive detectors only provide an indication of the temperature of the condensate transiting the steam trap.

The present invention overcomes the limitations of the prior art by providing a steam trap monitor for accurately measuring the quantity of energy passing a given point in the form of steam and condensate and comparing that value to the amount of energy which should be passing that point as condensate to provide an indication of the amount of energy being wasted in the steam system. Located downstream from the steam trap, the present invention is capable of detecting both phases (water and steam) and of accurately measuring the heat content of each.

OBJECTS AND SUMMARY OF THE INVENTION

Accordingly, it is an object of the present invention to detect leaks in a closed steam system.

It is another object of the present invention to provide an improved arrangement for monitoring the operation of a steam trap.

Yet another object of the present invention is to provide improved means for detecting loss of steam in a closed steam system via a failed steam trap.

A further object of the present invention is to detect a steam trap which has failed closed thus preventing condensate from being removed from a closed steam system.

A still further object of the present invention is to accurately measure steam energy in a closed steam system by measuring system total energy (condensate+steam) as well as condensate energy alone and substracting condensate energy from total system energy to arrive at an accurate measure of steam energy.

Another object of the present invention is to provide for the monitoring of steam trap operation downstream from the trap in a closed steam system.

The present invention contemplates the use of dual sensors in the adjacent downstream pipe from the steam trap, with one sensor being the combination of a hot finger and a thermocouple mill to measure condensate level and energy in the line and the second sensor being a cold finger to measure the total energy of the condensate and any steam in the line. Calculating the difference between these two values by appropriate signal processing means provides an indication of the steam downstream from trap and thus is an indication of energy lost from the steam system. The hot finger employs one or more thermocouples for indicating condensate level and energy, while the cold finger contains a mixture such as of water and alcohol having a lower boiling temperature than that of water. Vapor from the mixture is used to do work such as displacing an upper piston or expanding a bellows to a position indicating the total energy of the system. The steam trap monitor includes means for heat dissipation in the form of fins around the piston chamber and means for returning the liquid to the liquid chamber of the cold finger.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DESCRIPTION OF THE PREFERRED EMBODIMENT

Figure 1:
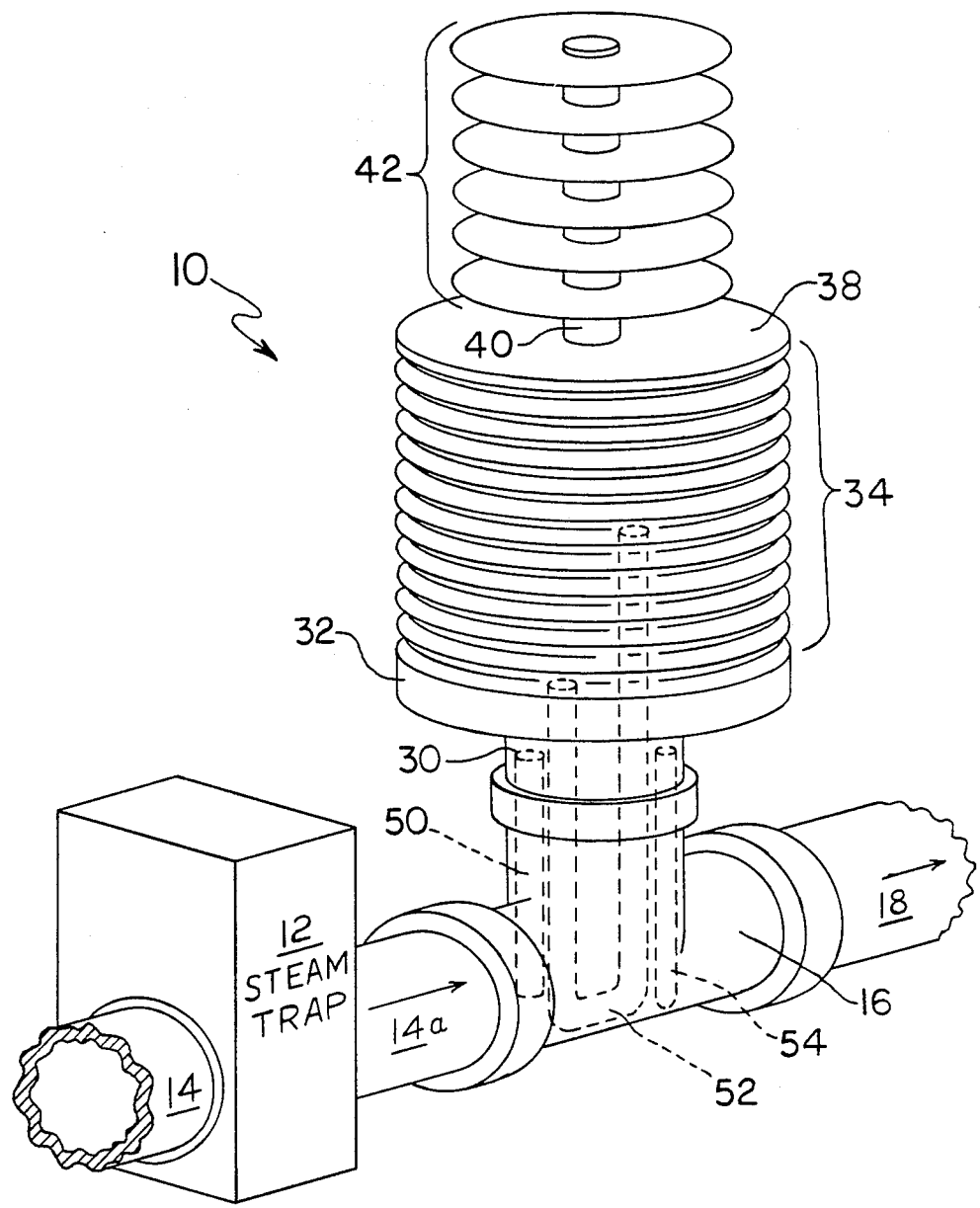
FIG. 1 is a perspective view shown partially in phantom of a steam trap monitor for use in a closed steam system in accordance with the present invention.
Figure 2:
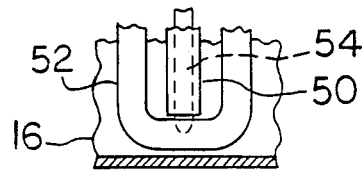
FIG. 2 is a lateral planar view of that portion of the steam trap monitor of FIG. 1 positioned within a pipe as viewed from a first side of the pipe.
Figure 3:
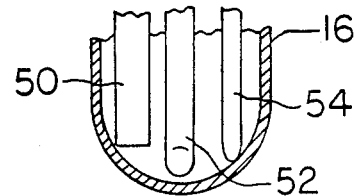
FIG. 3 is a planar view of that portion of the steam trap monitor of the present invention positioned within the pipe of FIG. 1 as viewed when looking downstream.
Figure 4:
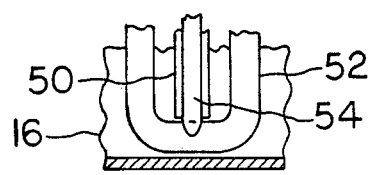
FIG. 4 is a lateral planar view of that portion of the steam trap monitor located within the pipe of FIG. 1 when viewed from the opposite side as that depicted in FIG. 2.

Referring to FIG. 1, there is shown a perspective view partially in phantom of a steam trap monitor 10 in accordance with the principles of the present invention. FIGS. 2, 3 and 4 illustrate various lateral views of that portion of the steam trap monitor 10 which extends into a steam pipe 14.

The steam trap monitor 10 is intended for use in a closed steam system having a steam pipe 14 to which is coupled a steam trap 12. The steam trap 12 may be of conventional design and operation and functions to remove condensate and air from the steam system while retaining live steam for use in a process. Because the steam trap monitor 10 of the present invention may be used with virtually any type of steam trap 12, the steam trap in FIG. 1 is merely illustrated as a block for simplicity.

The steam trap monitor 10 is adapted for insertion in and secure coupling to a "tee" fitting 16. The tee fitting 16 is adapted for secure coupling at a first end thereof to an intermediate steam pipe section 14a and at the other end thereof to a condensate return line 18. Secure, sealed coupling between the various pipe sections and the steam trap 12 and tee fitting 16 prevents escape of steam or condensate from the closed system. The condensate return line 18 directs condensate removed from the steam pipe 14 by the steam trap 12 to a source of steam generation such as a boiler (not shown for simplicity) for re-use in carrying out a process. Direction of flow of the steam and condensate within the closed steam system is shown by the arrows in FIG. 1.

Figure 5:
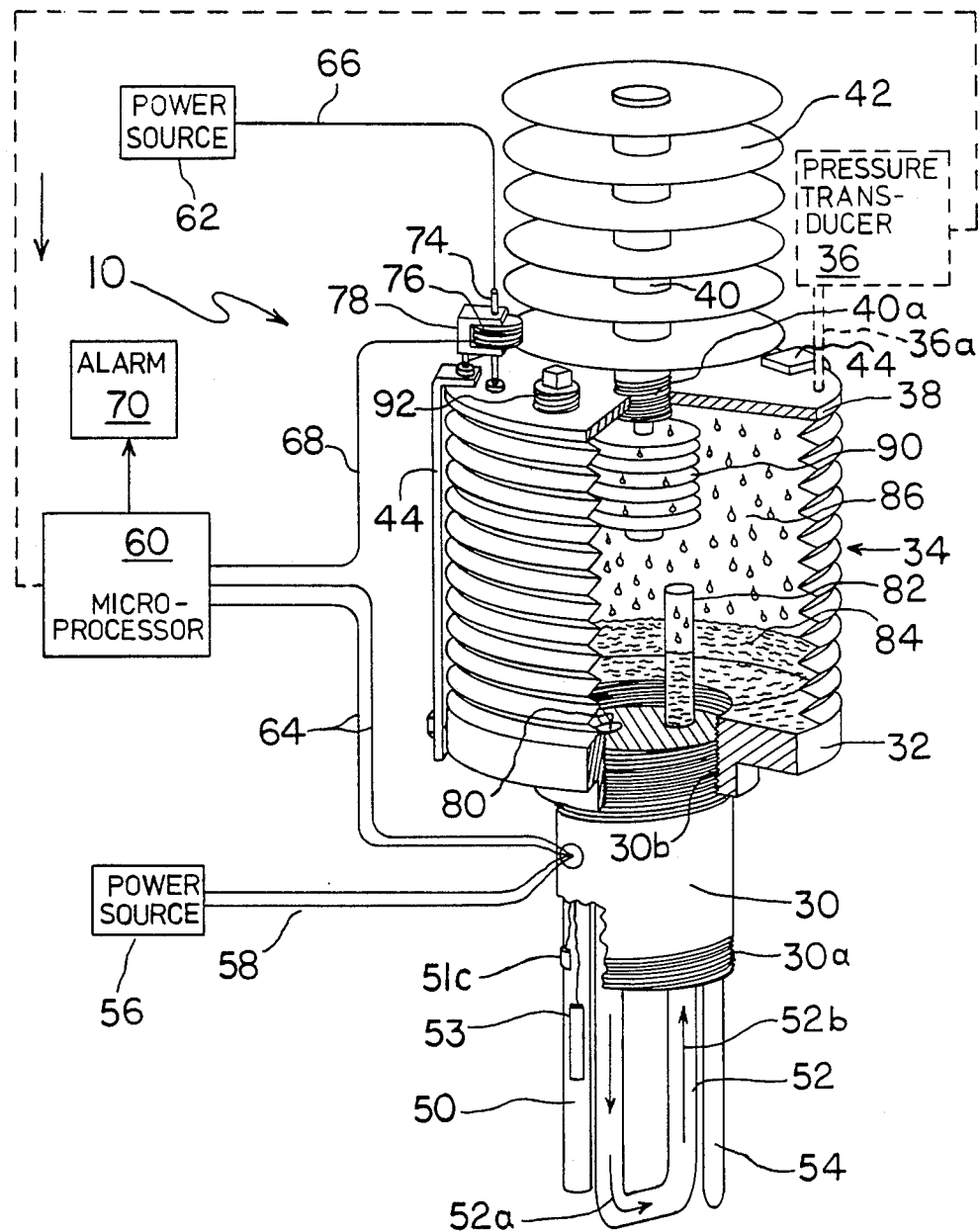
FIG. 5 is a combined simplified schematic and partially cutaway perspective view of the steam trap monitor of FIG. 1.

Referring to FIG. 5 as well as to FIGS. 1 through 4, the configuration and operation of the steam trap monitor 10 will now be described. The steam trap monitor 10 includes a generally cylindrical base 30 having lower and upper end outer threaded portions 30a and 30b. The base 30 is preferably comprised of a material having low thermal conductivity and is adapted to receive and threadably engage on the upper end thereof a threaded inner portion of a bellows base 32. Securely coupled to the bellows base 32 around the flat upper surface thereof is a bellows 34 comprised of a plurality of pleats to allow the bellows to expand and contract along its longitudinal axis. Mounted in a spaced manner around the outer peripheral portion of the bellows base 32 are a plurality of elongated retainers 44. The retainers 44 restrict lateral displacement of the bellows 34 and ensure that the bellows expands and retracts immediately above and in alignment with the bellows base 32. Coupled to the upper end portion of the bellows 34 is a washer-like bellows top section 38. Upper end portions of each of the retainers 44 engage the bellows top 38 when the bellows is fully extended and prevent further expansion of the bellows.

The bellows top 38 includes an upper threaded center aperture in its top section 38 for receiving and engaging the threaded lower end of a radiator support shaft 40. Positioned in a spaced manner along the length of the support shaft 40 are a plurality of metallic discs which, in combination, form a metal radiator 421. Coupled to and suspended from the lower end of the radiator support shaft 40 is a metal condenser 90 which also has a plurality of spaced discs along its length and thus has a configuration similar to that of the radiator 42. The condenser 90 is positioned within and aligned generally along the longitudinal axis of the bellows 34 which forms a closed, sealed structure expandable along its longitudinal axis.

Coupled to and extending downward from the base 30 of the steam trap monitor 10 are a cylindrical shaped hot finger 50, a U-shaped cold finger 52, and a cylindrical shaped thermocouple well 54. The hot finger 50 is comprised of a hollow metal structure and contains one or more thermocouples, only one of which thermocouple 51c is shown in FIG. 5 for simplicity, as well as a cartridge heater 53. The cartridge heater 53 is coupled to and energized by a first power source 56 via a first conductor 58. The thermocouples are coupled to a microprocessor 60 by means of a plurality of second conductors 64. The thermocouple well 54 is also preferably comprised of a hollow metal structure which contains a thermocouple (not shown) also coupled to the microprocessor 60 via one of the second conductors 64.

The cold finger 52 is preferably comprised of hollow metal tubing configured in a generally U-shape and contains a liquid with a lower boiling temperature than that of water. Such liquids as a water-alcohol mixture, pure alcohol or carbon tetrachloride may be used in cold finger 52, with a water-alcohol mixture used in describing the invention in the following paragraphs. The cold finger 52 is coupled to and continuous with a pair of ducts within the steam trap monitor's base 30 such that one end of the cold finger terminates in a liquid inlet 80 positioned on the upper end of the base while the other end of the cold finger is continuous with a low conductivity exhaust tube 82 extending upward from the upper end of the steam trap monitor's base. The upper end of the exhaust tube 82 is open and allows vapor from the boiling liquid mixture to escape from the U-shaped cold finger 52 into the expandable bellows 34.

Securely mounted to an upper end of one of the retainers 44 by means of a holder 78 is a coil 76. The coil 76 is also coupled to the microprocessor 60 by means of a fourth conductor 68. The coil 76 is further coupled to a second power source 62 via a third conductor 66. The second power source 62 applies a voltage across the coil 76 causing current to flow therein. Positioned within the coil 76 and securely mounted to the bellows top 38 is an armature 74 preferably comprised of iron or other highly electromagnetic material. The armature 74 is freely displaceable along its length within the coil 76 as the bellows 34 expands and contracts as its top 38 is vertically displaced in repsonse thereto. Threadably positioned within a second aperture in the bellows top 38 is a removable fill plug 92. The first and second power sources 56, 62 may be any conventonal source of alternating voltage. In fact, a common AC source with appropriate voltage level control circuitry may be used to energize both the cartridge heater 53 as well as the coil 76.

Figure 6:
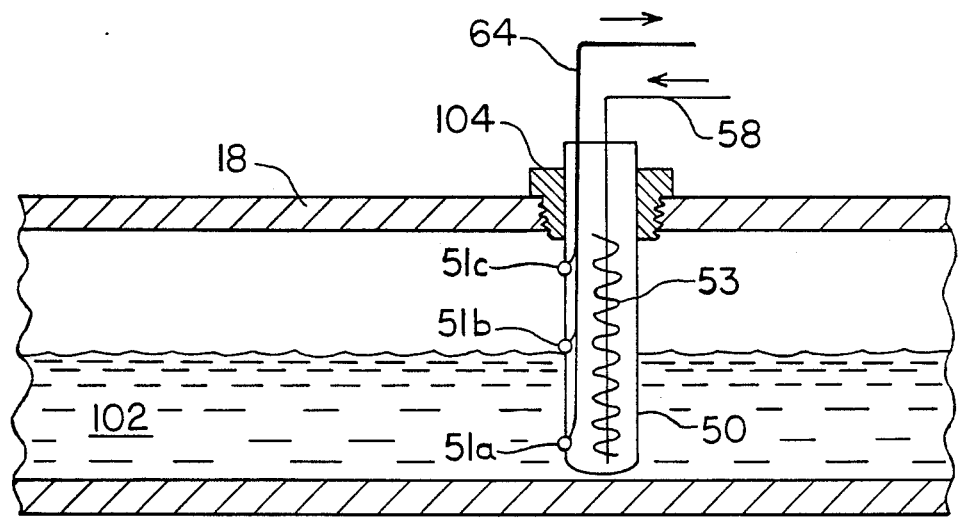
FIG. 6 is a sectional view of the hot finger sensor of the present invention as positioned in a condensate carrying pipe.

With reference to FIG. 6 as well as to figures discussed above, the operation of the steam trap monitor 10 of the present invention is not only detecting steam leakage through the steam trap 12 but also the extent of energy loss through the steam trap will now be described in detail. The amount of heat in the condensate 102 within the condensate return line 18 can be determined by measuring the quantity of condensate 102 (water) flowing and its temperature. In the present invention, water temperature is determined by the use of a thermometer or thermocouple within the thermocouple well 54. The quantity of condensate 102 is determined by the hot finger 50 which contains an electrical heating element 53 and a plurality of thermocouples 51a, 51b and 51c spaced along its length. The level of the condensate 102 within the condensate return line 18 is determined by the temperature sensed by the thermocouples 51a, 51b and 51c. The resistive heating element 53 heats up the hot finger 50 and depth of the condensate 102 determines from which poriton of the hot finger thermal energy is removed from the hot finger, with each of the aforementioned thermocouples providing an indiciation of this heat removal at various locations along the length of the hot finger 50. With the temperature and depth of the condensate 102 provided to the microprocessor 60, the microprocessor determines the thermal energy in the condensate. In another embodiment, the resistive heating element 53 is positioned above a single thermocouple wiithin the hot finger 50. In this embodiment, the resisitive heating element as well as the single thermocouple are both positioned above the condensate.

The hot finger 50 is positioned within the condensate return line 18 and extends substantially from the top to the bottom thereof. Input power is provided via the first conductor 58 to the resistive heating element 53, while second conductors 64 coupled to each of the thermocouples 51a, 51b and 51c provide respective output signals to the microprocessor 60. The hot finger is placed vertically in the horizontal condensate pipe 18, entering through the top surface thereof and terminating at the lower internal surface of the condensate pipe. The hot finger 50 is comprised of a suitable metal, such as copper or stainless steel, and is approximately ⅛ and ¼ inch in diameter. The resistive heating element 53 generates heat uniformly along the hot finger's length which is equal to the inside diameter of the condensate pipe 18. The plurality of thermocouples 51a, 51b and 51c are attached at the lower third, middle aand upper third of the hot finger 50. A suitable metal skin or casing is applied over the three thermocouples and their wire connectors which exit the condensate pipe 18 either through the steam trap monitor's base 30 or through a suitable pressure fitting 104 which is threadably coupled to and inserted in an aperture in an upper portion of the condensate return line.

Condensate (or water) depth is measured in terms of the temperature indications provided by the three thermocouples 51a, 51b and 51c to the microprocessor 60. For example, a high temperature indication at thermocouples 51b and 51c and a low temperature at the bottom thermocouple 51a indicates a low water flow. Low temperatures sensed by all three thermocouples indicates that the condensate return line 18 is filled with water. The microprocessor 60 to which the outputs of the three thermocouples 51a, 51b and 51c are provided via conductors 64 automatically computes the flow and quantity of heat attributable to the condensate flowing in the condensate return line 18.

To determine if live steam is leaking through the steam trap 12, the total heat flow in the condensate return line 18 is determined and the heat of the condensate 102 is subtracted from the total heat flow to provide the amount of heat due to the presence of steam in the condensate return line. If the total heat flow is equal to the condensate heat then no steam is leaking through the steam trap. The U-shaped cold finger 52 is used to determine the total heat within the condensate return line 18 just downstream from the steam trap 12. As in the case of the hot finger 50 which contains the three thermcouples 51a, 51b and 51c, the cold finger 52 enters the condensate return line 18 through the steam trap monotor's base 30 from the top of the return line and is oriented generally vertically. The cold finger 52 extends downward into the condensate return line 18 to a location adjacent to the inside lower surface of the return line. The cold finger 52 is comprised of a suitable material to withstand steam temperature and pressure and is thermally highly conductive. Typical materials for use in the cold finger 52 would be metal or ceramic. As indicated above, one end of the cold finger 52 is coupled to and continuous with an exhaust tube 82 extending upward from the upper surface of the steam trap monitor's base 30. The upper end of the exhaust tube 82 is open. The mixture of water and alcohol within the cold finger 52 is in the liquid phase in a first portion 51a of the cold finger and is converted to a vapor by the heat of the condensate and possibly steam within the condensate return line 18 such that a second portion 52b of the cold finger contains the alcohol/water mixture in the vapor phase. The heated water/alcohol vapor mixture forms a working vapor 86 within the steam trap monitor's bellows 34 causing upward expansion of the bellows. After the working vapor 86 performs work on the bellows 34 in expanding it resulting in loss of heat by the vapor, the vapor condenses in the form of a working fluid 84 in the lower portion of the bellows 34 and returns to the U-shaped cold finger 52 via a liquid inlet 80 within the steam trap monitor's base 30. The water/alcohol mixture within the cold finger 52 is thus cyclically vaporized by the heat of the condensate/steam in the condensate return line 18 and is allowed to condense to liquid form in the expandable bellows 34 and to return to the cold finger. Expansion of the bellows 34 provides a variable rate of heat dissipation to ensure that bellows expansion is limited and to allow the steam trap monitor of the present invention to operate over a wide thermal energy range.

Heat radiates from the surface of the bellows 34. Steam flowing in the condensate return line 18 condenses on the cold wall surface of the cold finger 52 thus giving up its latent heat and causes the water/alcohol mixture in the cold finger to vaporize. Vaporization of the water/alcohol mixture in the cold finger 52 results in an increase in pressure in the expandable portion, i.e., bellows 34, of the closed sytem. The amount of expansion is a measure of the total heat flowing in the water and steam within the condensate return line 18.

With the armature 74 movable within the coil 76 in response to the expansion and contraction of the bellows 34, the combination of the armature and coil forms as linear-variable differential transformer 72. With the coil 76 energized by the second power source 62, displacement of the armature 74 relative to and within the coil 76 will result in a change in the current within the coil. With the coil 76 coupled to the miscroprocessor 60 via a fourth conductor 68, a signal representing the change in coil current is provided from the coil to the microprocessor, which signal coresponds to the displacement of the bellows 34 due to its expansion arising from the work performed by the working vapor 86. The signal provided by the coil 76 to the microprocessor 60 therefore represents and corresponds to the heat (steam+condensate) within the condensate return line.

With a first input provided to the microprocessor 60 from the coil 76 representing the total energy of the condensate and steam (if any) and a second input from the thermocouples within the hot finger 50 as well as in the thermocouple well 54 representing the heat of the condensate 102, the microprocessor substracts the second signal measured energy from the first signal measured energy to determine the energy of the steam within the condensate return line 18. The microprocessor 60 may be programmed in a conventional manner to compare the heat of the steam within the condensate return line 18 to a predetermined heat value representing system measurement error and to activate an alarm 70 if the heat of the steam exceeds this predetermined heat value. Actuation of alarm 70, which may be either an aural or visual alarm, provides a warning of a failure of the steam trap 12 and the need to replace or repair it. The present invention contemplates the use of a conventional microprocessor 60 which could be easily programmed by one skilled in the art to perform the signal comparison and alarm actuation functions described. In addition, the present invention contemplates the coupling of a plurality of the inventive steam trap monitors 10 to a single microprocessor 60 which would provide a monitoring capability for all steam traps at a facility and afford central surveillance of all the traps in a closed steam system.

The expandable bellows 34 provides for variable rate heat dissipation in the steam trap monitor. Thus, the bellows 34 is not permitted to continuously expand in response to the presence of steam in the condensate return line 18, but rather reaches an expansion limit as the volume of the bellows 34 increases to a predetermined limit. As the bellows 34 increases to this limit, increased internal surface area of the bellows provides a larger condensation surface for the working vapor 86 therein which is increasingly converted to liquid and collects in the lower portion of the bellows. Direct coupling by means of the support shaft 40 between the external radiator 42 and the metal condenser 90 within the bellows 34 allows the radiator to function as a heat leak and provide a constant rate of heat dissipation for the bellows. A fill plug 92 threadably positioned within an aperture in the bellows top 38 permits the alcohol/water mixture to be added to the bellows 34.

In another embodiment, the change in volume of a bellows is not used as an indication of total system energy, but rather a change in pressure with the volume maintained constant provides and indication of total system energy. In this arrangement, a pressure transducer 36 (shown in dotted line form in FIG. 5) is coupled via an air tube 36a to the upper surface of the bellows 34 which is maintained in a fixed configuration and size by the retainers 44. The change in pressure within the bellows 34 arising from vaporization of the water/alcohol mixture is measured by the transducer 36 which provides an appropriate signal to the micoprocessor 60. In still another embodiment, the rate of change of the volume of the bellows 34 rather than the difference between its initial and final volumes may be used as a measure of system total energy.

There has thus been shown an arrangement positioned downstream from a steam trap for monitoring steam trap operation by measuring total system energy (condensate+steam) as well as condensate energy only and, by subtracting one value from the other, determining the steam energy in the system. The presence of steam in the condensate return line as well as the absence of condensate therein, as detected by the present invention, provides an indication that the steam trap has failed and should be replaced.

While particular embodiments of the present invention have been shown and described it will be obvious to those skilled in the art that changes and modifications may be made without departing from the invention in its broader aspects. For example, while the tee fitting 16 is shown as having a circular cross section it may in some cases be desirable to provide a square or rectangular cross section where the steam trap monitor is inserted in the condensate return line. These latter cross sectional shapes would facilitate calibration of the system as well as changing the size of the sensors and the volume of the belllows to accomodate different steam system and steam trap operating parameters. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. For use in a closed steam system, apparatus coupled to a stream trap by means of a pipe and located downstream therefrom for monitoring said steam trap, said apparatus comprising:

first sensing means in the pipe for determining the heat energy of a condensate flow in the pipe;

second sensing means in the pipe for determining the heat energy of the condensate flow and any flow steam in the pipe; and means coupled to said first and second sensing means for determining the difference between the heat energy of the condensate flow and steam flow and the heat energy of just the condensate flow to detect the presence of any steam in the pipe in monitoring operation of the steam trap.

2. The apparatus of claim 1 wherein the pipe is a condensate return line.

3. The apparatus of claim 1 wherein said first sensing means includes means for measuring the volume of condensate flowing in the pipe and means for measuring the temperature of the condensate in the pipe.

4. The apparatus of claim 3 wherein said means for measuring the volume of condensate flowing in the pipe includes a hot finger and said means for measuring the temperature of the condensate includes a thermocouple well.

5. The apparatus of claim 4 wherein said hot finger includes a heating element for heating said hot finger and at least one thermocouple for sensing the rate at which heat is removed from said hot finger by the condensate in the pipe.

6. The apparatus of claim 5 wherein said hot finger further includes a plurality of thermocouples positioned in spaced relation along the length of said hot finger and aligned in a generally vertical array.

7. The apparatus of claim 5 wherein said heating element is positioned abovesaid at least one thermocouple in said hot finger and wherein said at least one thermocouple is positioned generally above the condensate level in the pipe and a distal end of said hot finger is positioned in closely spaced relation to a bottom inner portion of the pipe.

8. The apparatus of claim 1 further comprising a power source for energizing said first sensing means.

9. The apparatus of cliam 1 wherein said second sensing means includes a cold finger containing a vaporizing working fluid and means for measuring the response of said working fluid to elevated temperatures in the pipe.

10. The apparatus of claim 9 wherein said cold finger comprises a generally U-shaped hollow tube extending downward into the pipe.

11. The apparatus of claim 10 wherein said working fluid comprises a mixture of water and alcohol.

12. The apparatus of claim 9 wherein said means for measuring the response of said working fluid to elevated temperatures includes a fixed volume structure for receiving said working fluid after being vaporized by said elevated temperatures and means for measuring the increase in pressure in said fixed volume structure following vaporization of said working fluid.

13. The apparatus of claim 12 wherein said means for measuring the increase in pressure in said fixed volume structure comprises a pressure transducer coupled to said third means.

14. The apparatus of claim 9 wherein said means for measuring the response of said working fluid to elevated temperatures includes an expandable bellows and expansion detection means coupled to said third means for detecting expansion of said bellows and for providing a corresponding signal to said third means.

15. The apparatus of claim 14 wherein said expansion detection means includes an electromagnetic detector.

16. The apparatus of claim 16 wherein said electromagnetic detector comprises a linear variable differential transformer.

17. The apparatus of claim 16 wherein said linear variable differential transformer includes a coil coupled to said third means and a conductive armature electromagnetically coupled to said coil and mounted to said bellows and energized by a power source.

18. The apparatus of claim 14 further comprising radiating means coupled to said bellows for dissipating heat from said bellows at a constant rate.

19. The apparatus of claim 18 further comprising condensation means coupled to said radiating means and position within said bellows for facilitating condensation of said working fluid from vapor to liquid.

20. The apparatus of claim 19 wherein said radiating means and said condensation means are each comprised of a respective elongated, linear shaft with a plurality of discs positioned in spaced relation along the length thereof.

21. The apparatus of claim 1 wherein said means for determining said heat energy difference includes a microprocessor.

22. The apparatus of claim 1 further comprising alarm means coupled to said means for determining said heat energy difference and for providing an indication of the presence of steam in the pipe.

* * * * *